United States Patent [19]

Berry

[11] 4,210,152
[45] Jul. 1, 1980

[54] METHOD AND APPARATUS FOR MEASURING AND CONTROLLING THE OUTPUT POWER OF A SHORTWAVE THERAPY APPARATUS

[75] Inventor: Fred M. Berry, Johnson County, Kans.

[73] Assignee: International Medical Electronics Ltd., Kansas City, Mo.

[21] Appl. No.: 901,854

[22] Filed: May 1, 1978

[51] Int. Cl.² ............................................. A61N 1/40
[52] U.S. Cl. ................................. 128/422; 128/804
[58] Field of Search ............... 128/404, 405, 413, 421, 128/422, 423 R, 303.13, 303.14, 303.17, 303.18, 804, 783; 219/10.77

[56] References Cited

U.S. PATENT DOCUMENTS

| 2,698,622 | 1/1955 | Martens | 128/422 |
|---|---|---|---|
| 2,752,496 | 6/1956 | Martens | 128/422 X |
| 3,127,895 | 4/1964 | Kendall et al. | 128/422 |
| 3,299,892 | 1/1967 | Kendall et al. | 128/421 |
| 3,329,148 | 7/1967 | Kendall | 128/422 |
| 3,543,762 | 12/1970 | Kendell | 128/422 |
| 3,566,877 | 3/1971 | Smith et al. | 128/422 |
| 3,800,802 | 4/1974 | Berry et al. | 128/422 |
| 3,923,063 | 12/1975 | Andrews et al. | 128/303.14 |
| 3,930,193 | 12/1975 | Komrumpf et al. | 219/10.77 X |
| 4,068,292 | 1/1978 | Berry et al. | 128/404 X |
| 4,069,827 | 1/1978 | Dominy | 128/422 |

Primary Examiner—Lee S. Cohen
Attorney, Agent, or Firm—Lowe, Kokjer, Kircher, Wharton & Bowman

[57] ABSTRACT

This invention discloses a method and apparatus for accurately measuring and controlling the amount of power being absorbed by a load within the irradiating region of a diathermy applicator head. A desired power setting is initially preset into the diathermy apparatus. Thereafter, the diathermy apparatus is keyed on for a predetermined duty cycle causing RF energy to be generated within the applicator head during this time period. The level of power being absorbed by the load is then ascertained by measuring voltage and current flow in the head during the duty cycle. In the preferred embodiment of the invention, the electrostatic energy generated in the applicator head is attenuated by an electrostatic shield. Attenuation of the electrostatic energy improves the stability of the diathermy apparatus by significantly reducing electrostatic coupling between the applicator head and its attendant load. Once the electrostatic field is eliminated, the level of power being applied to the applicator head accurately represents the level of power being absorbed by the load within the irradiating region of the head. The diathermy apparatus is also provided with circuitry for keeping the applicator head in electrical resonance thereby improving the power measurement by ensuring that the voltage and current are locked in phase. The measured level of power is then multiplied by the duration of the duty cycle to provide a figure representative of the total amount of power being absorbed by the load. This figure is compared with the preset level and the duty cycle is adjusted accordingly.

36 Claims, 6 Drawing Figures

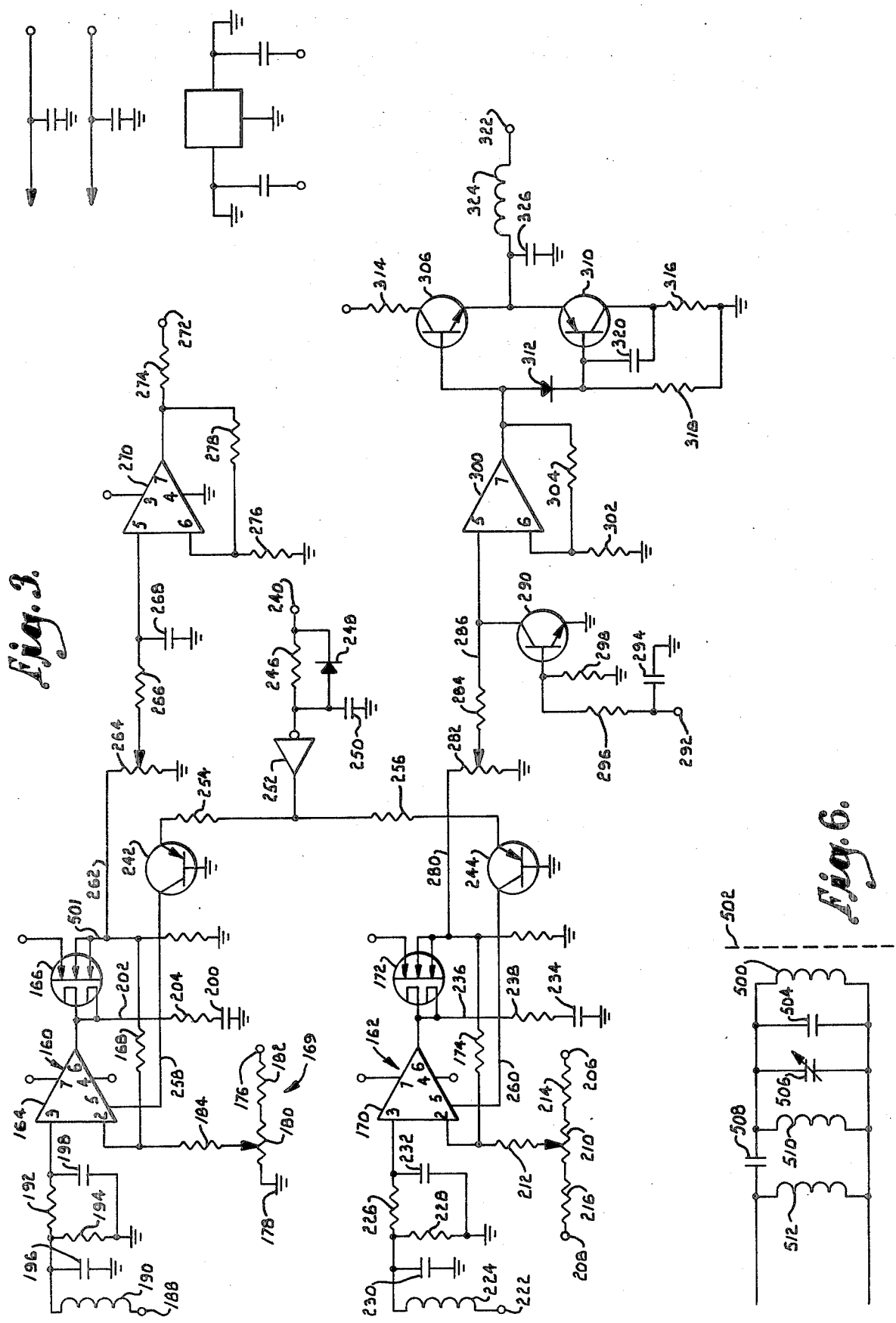

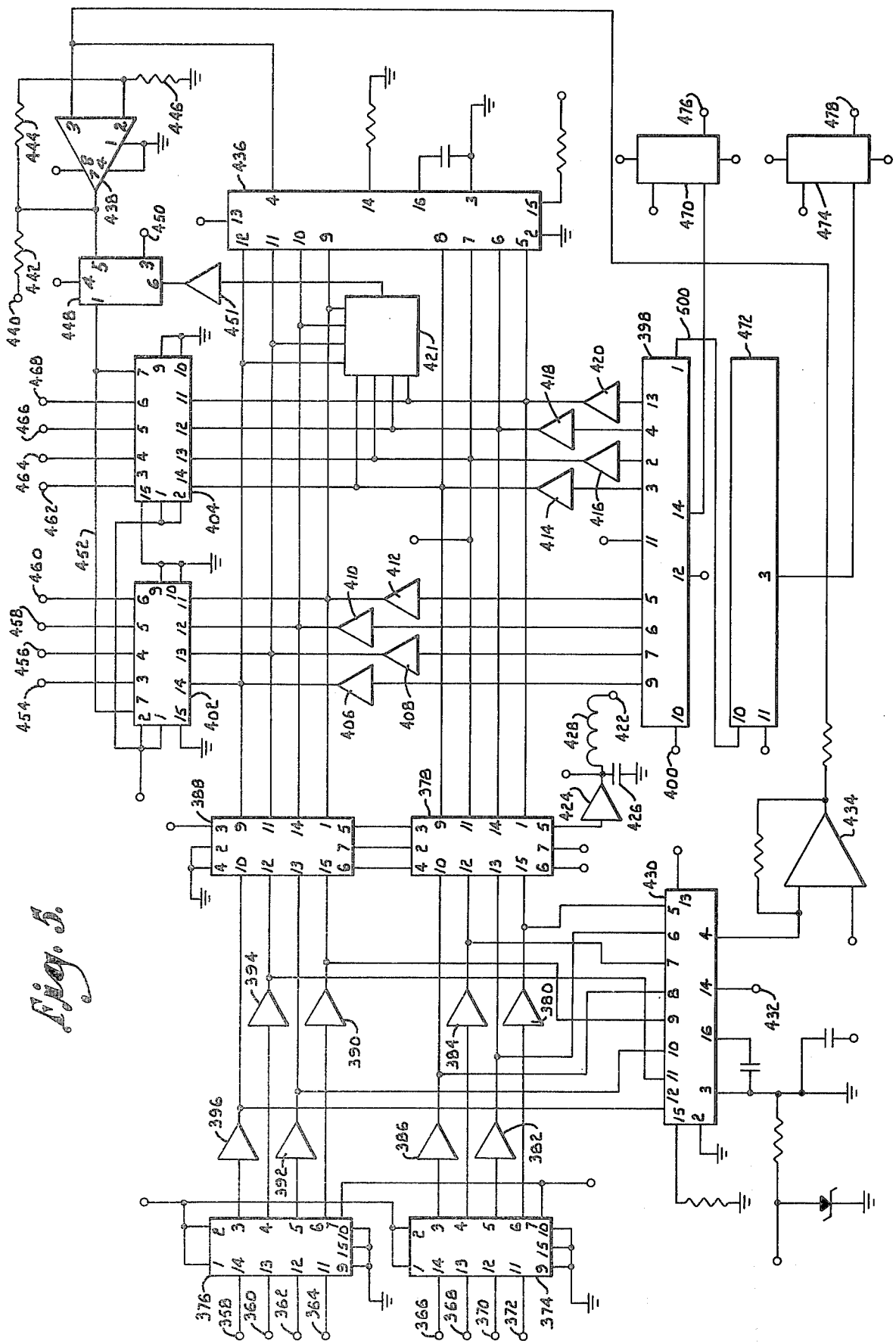

METHOD AND APPARATUS FOR MEASURING AND CONTROLLING THE OUTPUT POWER OF A SHORTWAVE THERAPY APPARATUS

BACKGROUND AND SUMMARY OF THE INVENTION

This invention relates in general to a diathermy apparatus which therapeutically heats internal body tissue by irradiating the tissue with RF energy. In particular, the present invention discloses a method and apparatus for accurately measuring and controlling the amount of RF power being absorbed by the body tissue within the irradiating region of the diathermy apparatus.

Medical diathermy involves the use of high frequency electric currents for the therapeutic treatment of body tissues. This technique involves the transcutaneous transmission of high frequency energy to internal body tissues. The irradiated RF energy generates within the internal body tissue heat which has a therapeutic effect. This deep heating action produced by the diathermy apparatus is used to treat a number of varied ailments.

A diathermy apparatus typically generates high frequency electric currents which are provided to an applicator head for controllable application to the body tissue to be treated. The high frequency currents produced in a diathermy apparatus typically have a standard frequency of 27.12 megahertz which is within the permissable frequency range allocated for diathermy service. At this frequency, nerves and muscles are not adversely stimulated by the radiated energy and the temperature produced in the internal body tissue is well below that required to destroy the tissue or impair its vitality.

The applicator head includes a radiating electrode which is comprised of an induction coil that generates electromagnetic and electrostatic energy in response to the high frequency electric currents flowing through the electrode. The generated electromagnetic and electrostatic energy is then controllably applied by the applicator head to the body of the patient. This energy causes heat to be generated in the internal body tissue which is within the irradiating region of the head. Prior art diathermy devices are extremely erratic in operation. The operating parameters of these devices tend to vary widely making it impossible to accurately measure and control the level of power being absorbed by the treated body tissue.

My invention provides a unique method and apparatus for accurately measuring and controlling the amount of RF power being absorbed by the body tissue within the irradiating region of the diathermy apparatus. In particular, the present invention performs two unique operations. The first part of my invention deals with a unique method and apparatus for measuring the level of power actually being absorbed by the body tissue within the irradiating region of the applicator head. The second part of this invention describes a unique method and apparatus for using the measured power to accurately control the amount of power being absorbed by the body tissue.

The level of power being absorbed by the body tissue within the irradiating region of the applicator is ascertained by measuring the level of current being provided to the applicator head. Since the voltage is always a constant value, the level of power being irradiated by the applicator head is only a function of current. In order to ensure the accuracy of the power measurement, the current must be kept in phase with the voltage. The introduction of a reactive load into the irradiating region of the applicator head causes the phase angle between the current and voltage to vary from zero. However, if the applicator head is maintained in electrical resonance, the load on the head appears to be merely resistive so that there is no reactive component to cause a shift in phase between the current and voltage.

It has been found that the elimination of the electrostatic field through the use of an electrostatic shield significantly improves the operating efficiency of the diathermy apparatus and the accuracy of the power measurement. A general description of the design and use of an electrostatic shield is given and described in U.S. Pat. No. 4,068,292 to Berry, et. al. entitled "Electrostatic Shield for Diathermy Treatment Head". This patent was issued on Jan. 10, 1978 and is incorporated by reference herein.

The interposition of an electrostatic shield between the generating electrode in the applicator head and the treated body tissue significantly reduces the electrostatic (capacitive) coupling between the body tissue and the applicator head thereby making the reactive parameters of the head less responsive to the surface characteristics of the load within irradiating region of the head. By eliminating capacitive coupling between the applicator head and the body tissue, the operating parameters of the diathermy apparatus no longer vary erratically in response to the surface characteristics of the load within the irradiating region of the head. Since the operating parameters of the device do not vary in response to the surface characteristics of the load, the level of power being provided to the applicator head only varies in response to the level of power actually being absorbed by the treated body tissue. While the introduction of body tissue into the irradiating region of the applicator head still causes some minor disturbances in the electrical operation of the power generating equipment, these disturbances are very small in magnitude and can be accurately measured. Furthermore, these minor disturbances are predictable and can be accounted for during the power computation.

Elimination of the electrostatic field also stabilizes the operation of the diathermy apparatus because the applicator head is less likely to be detuned from resonance upon the introduction of a load into the irradiating region of the head. Therefore, it is easier to keep the current and voltage locked in phase thereby greatly enhancing the operation of the diathermy apparatus and improving the accuracy of the power measurement.

The present invention includes a current sampling circuit which accurately measures the level of current being provided to the applicator head. For convenience, the current sampling circuit is located at a point which is exactly a half-wave away from the radiating electrode in the applicator head. This circuit measures the level of current being provided to the applicator head and produces a DC voltage signal having a voltage representative of the amplitude of the measured current. The current sampling circuit is also equipped with a phase detector which senses the phase difference between the current and voltage being provided to the applicator head. The phase detector provides a voltage signal representative of the difference in phase between these two signals. This voltage signal is then supplied to a servo motor which controls a tuning element in the applicator head. This tuning element is varied in order to keep the applicator head in electrical resonance thereby maintaining phase lock between the sensed current and voltage.

The amount of power being absorbed by the treated body tissue is accurately controlled in the present invention through a technique called "Duty Cycle Modulation". The duty cycle is the time period within a set repetition period during which the diathermy apparatus is activated. During each repetition period, the diathermy apparatus is keyed on for a prescribed period of time which is equal to the duty cycle. Since the level of absorbed power is dependent upon the characteristics of the load, the duration of the duty cycle must be varied to make total power correspond with the desired power setting.

The present invention is provided with a keying and computing circuit which keys on the diathermy apparatus during the duty cycle and computes total power by multiplying the established duty cycle by the DC voltage signal representative of the measured current. A signal representative of total amount of power being absorbed by the load is then provided to a control circuit where it is compared with a preset power value. The control circuit then adjusts the duty cycle accordingly.

It is therefore an object of the present invention to provide a method and apparatus for accurately measuring the level of power being absorbed by a load within the irradiating region of a diathermy applicator head.

Another object of the present invention is to provide a method and apparatus for measuring the level of power being absorbed by a load within the irradiating region of a diathermy applicator head which automatically adjusts for shifts in the reactive parameters of the applicator head thereby always keeping the head in electrical resonance.

Another object of the present invention is to provide a method and apparatus for measuring the level of power being absorbed by a load within the irradiating region of a diathermy applicator head wherein the applicator head is maintained in electrical resonance regardless of the surface characteristics of the load thereby significantly improving the operating stability of the diathermy apparatus.

A further object of the present invention is to provide a method and apparatus for accurately measuring the level of power being absorbed by a load within the irradiating region of a diathermy applicator head wherein the applicator head is maintained in electrical resonance regardless of the surface characteristics of the load so that the level of power being provided to the applicator head accurately represents the level of power being absorbed by the load.

A further object of the present invention is to provide a method and apparatus for measuring the level of power being applied to a load within the irradiating region of a diathermy applicator head wherein the level of power being absorbed by the load is accurately ascertained by measuring the voltage and current being provided to the applicator head.

It is an additional object of the present invention to provide a method and apparatus for accurately controlling the amount of power being irradiated by a diathermy applicator head wherein the amount of power being irradiated is controlled by means of a technique referred to as "Duty Cycle Modulation."

It is a further object of the present invention to provide a method and apparatus for accurately controlling the amount of power being irradiated by a diathermy applicator head by producing a duty cycle of the appropriate duration.

Another object of the present invention is to provide a method and apparatus for accurately controlling the amount of power being irradiated by a diathermy applicator head wherein the duration of the duty cycle is varied to control the amount of power being provided to the load regardless of the surface characteristics of the load.

It is a further object of the present invention to provide a method and apparatus for accurately controlling the amount of power being irradiated by a diathermy applicator head which compensates for internal power losses in the applicator head.

Other and further objects of this invention, together with the features of novelty appurtenant thereto, will appear in the course of the following description.

DETAILED DESCRIPTION OF THE INVENTION

In the accompanying drawings which form a part of the specification and are to be read in conjunction therewith and in which like reference numerals are employed to indicate like parts in the various views:

FIG. 3 is a detailed schematic diagram of the sample and hold portion of the sampler circuit shown in FIG. 1;

FIG. 5 is a schematic diagram of the keying and computing circuit shown in FIG. 1; and FIG. 6 is a schematic diagram of the applicator head.

Figure 1:
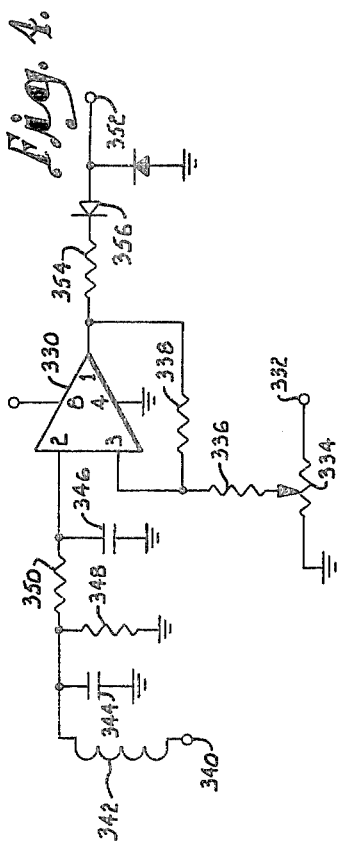
FIG. 1 is a block diagram of the diathermy apparatus of the present invention.

The overall operation of the present invention can be best described by referring to FIG. 1. As shown in FIG. 1 AC power is applied to the diathermy apparatus by means of an AC power line 10. This line supplies AC power to a power supply circuit 12 which transforms the incoming power signal into operation power for the various components of the diathermy apparatus.

An RF power amplifier 14 is provided to generate the high frequency electric currents needed to produce the RF energy irradiated by the applicator head 16. The RF power amplifier 14 is comprised of a crystal oscillator having a standard frequency of 27.12 megahertz which is within the frequency range allocated for diathermy service. This circuit also includes an amplifier stage which raises the power of the RF signal produced by the crystal oscillator to an appropriate level. An impedance transforming network in the RF power amplifier interconnects this circuit with a transmission line 18. The impedance transforming network matches the impedance of the RF power amplifier with the impedance of the transmission line without varying the relative phase of the voltage and current between these two points. Finally, the RF power amplifier is equipped with a keying circuit which controls the time period during which an RF signal is outputted by the RF power amplifier.

The applicator head 16 is electrically coupled to the RF power amplifier 14 by means of transmission line 18. A pi matching network is used to connect the head of the transmission line. The circuit is an impedance transforming network which matches the impedance of the line with that of the head without causing a shift in the relative phase of the current and voltage. Transmission line 18 has an electrical length equal to a whole multiple of a half-wave length. Since the electrical length of this transmission line is equal to a whole multiple of a half-wave, the voltage and current present in the applicator head are reflected back to the RF power amplifier unchanged. However, the impedance in the head is reflected back to the RF power amplifier as a ratio of the actual impedance in the head because of the impedance transforming network.

The applicator head 16 is coupled to the RF power amplifier such that the head experiences a maximum impedance when there is no load in its irradiating region and a minimum impedance when it is fully loaded. The value of the minimum and maximum head impedance is a function of the operating parameters of the RF power amplifier and the applicator head with the ratio between these two values representing the amount of head loss at a particular power level. Head loss is the amount of power dissipated by the applicator head because of internal power losses. This power is normally dissipated in the form of heat. The ratio between the maximum and minimum impedance is constant over the entire power range and is accounted for in the power computation. For example, if the applicator head produces at its connecting terminals a maximum impedance of 500 ohms and a minimum impedance of 50 ohms, 10% of the power applied to the applicator head at any level of power is dissipated as head loss, since the ratio between these two levels is 10 to 1.

The applicator head is provided with an inductive coil which generates electrostatic and electromagnetic energy in response to the high frequency currents provided to it from the RF power amplifier. In the preferred embodiment of this invention, the applicator head is equipped with an electrostatic shield for attenuating electrostatic energy. The electrostatic shield is interpositioned between the inductive coil in the head and the body of the patient being treated. Through attenuation of electrostatic energy, the operating efficiency of a diathermy apparatus is significantly improved. In particular, the deleterious surface heating effect which is produced primarily by the electrostatic field is virtually eliminated while the deep heating action of the diathermy apparatus is not impeded. A description of the design and use of an electrostatic shield is taught in U.S. Pat. No. 4,068,292 to Berry et. al., entitled "Electrostatic Shield for Diathermy Treatment Head" and issued on Jan. 10, 1978.

Attenuation of the electrostatic field also reduces electrostatic (capacitive) coupling between the patient's body and the applicator head. This capacitive coupling causes the reactive parameters of the treatment head to vary in response to the surface characteristics of the load within the irradiating region of the head. Variation of these reactive parameters produces a detuning effect in the applicator head which causes the magnitude of the generated field to vary erratically thereby making it extremely difficult to control the output power of the diathermy apparatus and to predict the level of power actually being absorbed by the treated tissue. By reducing capacitive coupling between the applicator head and the patient's body, the applicator head is less likely to be detuned from resonance upon introduction of a load into the irradiating region of the head. In this way, the operation of the diathermy apparatus is stabilized under various loading conditions thereby making it possible to control and predict the level of power being absorbed by the treated tissue.

Even though the interposition of an electrostatic shield between the inductive coil in the applicator head and the body tissue being treated significantly improves the stability of the diathermy apparatus, the operation of the diathermy apparatus still varies somewhat upon introduction of a load into the irradiating region of the head. However, this variation in operation is not erratic and is predictable since it is directly proportional to the level of power being absorbed by the load. As mentioned above, the magnitude of this variation is called head loss and is proportionally related to the level of power being absorbed by the load as a ratio of the maximum head impedance to the minimum head impedance and is accounted for in the power measurement.

Once the electrostatic field is eliminated, the level of power being absorbed by the treated tissue is ascertainable by measuring the level of the current and voltage being provided to the induction coil in the applicator head. Since the voltage is constant, the power being absorbed by the treated tissue is strictly a function of the current being provided to the induction coil in the applicator head. The current and voltage must be in phase in order to accurately measure them. In order to maintain a zero phase angle between the voltage and current, the applicator head must be maintained in electrical resonance. When the applicator head is in resonance, the impedance of the head is purely resistive thereby ensuring that the current and voltage are in phase. The applicator head is equipped with a tuning element which is adjusted to keep the applicator head in electrical resonance thereby maintaining a zero phase angle between voltage and current.

A sampler circuit 20 is provided to measure current flow within the applicator head 16. For convenience, this circuit is located at a point which is exactly a half-wave length away from the induction coil in the applicator head. It is a well known property of transmission lines that impedance, voltage and current are repeated every half-wave length. Therefore, the value of current measured by the sampler circuit 20 at the half-wave point is proportional to the current in the applicator head.

Sampler circuit 20 includes a current measuring circuit which measures the current being provided from the RF power amplifier 14 to the applicator head and produces a DC voltage signal representative of the amplitude of the measured current. The DC voltage signal representative of the measured current is then processed in a sample and hold circuit. The sample and hold circuit samples the voltage of this DC voltage signal during the duty cycle and stores the sampled voltage until this signal is once again sampled during the next duty cycle. The sample and hold circuit also filters, centers and amplifies the sampled signal to produce the current sample signal which is represented at output line 22. Through proper centrifugal calibration of the sampled signal in sample and hold circuit, the amount of head loss at any power level is automatically accounted for thereby providing a current sample signal which is an accurate measure of the level of power actually being absorbed by the load.

The current sampler is also equipped with a phase detector circuit which monitors the phase relationship between the voltage and current being provided to the applicator head. The phase detector generates a phase comparison signal which is provided to another sample and hold circuit. This sample and hold circuit processes the phase comparison signal to produce a phase control signal which is a DC voltage signal having a voltage related to the difference in phase between the monitored current and voltage. This phase control signal is represented at output line 24 and is provided to a servo motor which controls the tuning element in the applicator head. In this way, the applicator head is kept in electrical resonance thereby ensuring that the voltage and current provided to the applicator head are always in phase. Finally, current sampler 20 is equipped with an overload sensing circuit which automatically shuts off the diathermy apparatus if an overload condition occurs.

The diathermy apparatus of the present invention controls the amount of power being absorbed by the treated tissue by means of a technique referred to as "Duty Cycle Modulation." The duty cycle is the period of time during each repetition period wherein the RF power amplifier is supplying RF energy to the applicator head. During each repetition period, the RF power amplifier is keyed on for a period of time equal to the duty cycle. A figure representative of the total amount of power being absorbed by the load is obtained by multiplying the measured level of power provided to the applicator head by the duration of the duty cycle.

A digital controller and display circuit 26 is provided to control the overall operation of the diathermy apparatus. The primary function of this circuit is to establish a duty cycle of the appropriate duration. A particular power setting is initially programmed into the controller and display circuit. Upon activation of the diathermy apparatus, the digital controller and display circuit establishes a duty cycle of minimum duration. Thereafter, this circuit compares the figure represenative of total power with the programmed power setting and adjusts the duration of the duty cycle accordingly. If the total power figure is less than the programmed power setting, the duration of the duty cycle is lengthened by an incremental amount. The duration of the duty cycle is continuously lengthened until the figure representative of total power is equivalent to the power setting. Similarly, the duration of the duty cycle is shortened by an incremental amount if the total power figure is greater than the programmed power setting. The digital controller and display circuit is also capable of performing a number of additional functions such as displaying the figure representative of total power, controlling the time period during which the diathermy apparatus is activated, and changing the power setting after a prescribed period of time. It should be pointed out that the number of functions performed by digital controller and display circuit 26 is variable in accordance with the desired level of sophistication of the device. In the preferred embodiment, this circuit is comprised of a microprocessor which is programmed to perform the desired functions. However, it is also possible to fabricate this circuit from conventional logic circuitry using standard logic design techniques.

A keying and computing circuit 28 is provided to key on the RF power amplifier during the duty cycle and to derive a figure representative of the total power. The duty cycle selected by the digital controller and display circuit 26 is provided to the keying and computing circuit as represented by line 30. Thereafter, the keying and computing circuit activates the RF power amplifier as represented by key line 32 for the duration of the duty cycle. The keying and computing circuit then multiplies the current sample signal by the duty cycle to obtain a figure indicative of total power. The total power figure is then sent to the digital controller and display circuit where it is compared with the level of power programmed into this circuit.

Figure 2:
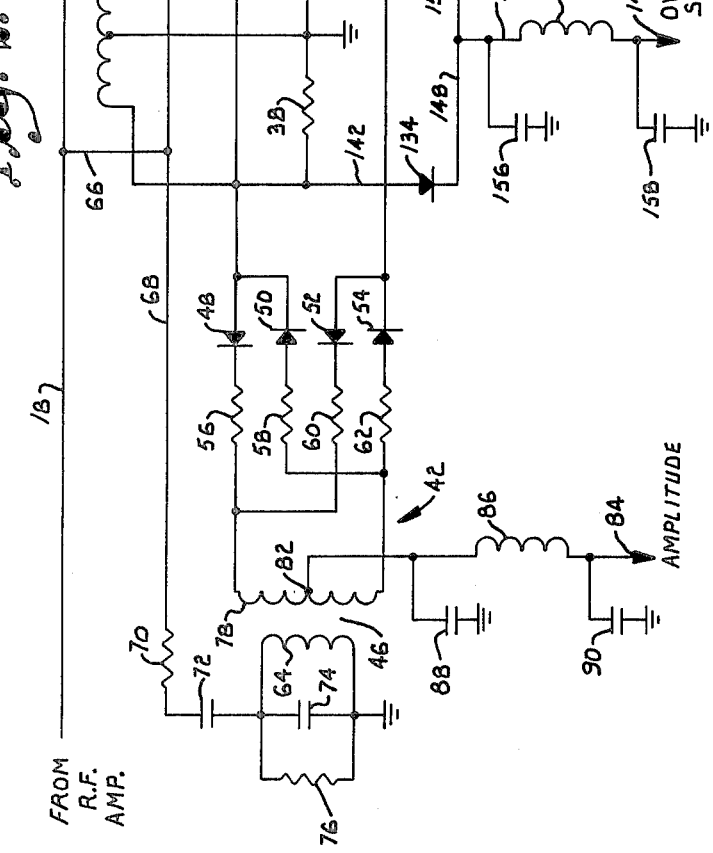
FIG. 2 is a schematic diagram of the current measuring, phase detector and overload sensing portion of the sampler circuit shown in FIG. 1.

Referring now to FIG. 2, the current measuring circuit, phase detector circuit, and overload sensing circuit of sampler circuit 20 are shown in this figure. This portion of the sampler circuit includes current measuring circuitry for measuring the current provided to the applicator head, a phase detector for monitoring the phase relationship between the measured voltage and current, and overload sensing circuitry for detecting an overload condition.

A current transformer 36 is located at a point which is exactly a half-wave length away from the inductive coil in the applicator head. The current transformer is loaded by a pair of resistors 38 and 40 which are of equal resistance. The voltage produced across these two resistors is provided to a pair of bridge demodulators which are generally designated by the numerals 42 and 44. The first bridge demodulator represents the current measuring circuit and is comprised of transformer 46, diodes 48, 50, 52 and 54, and resistors 56, 58, 60 and 62. Transformer 46 has a primary coil 64 which receives a voltage signal from transmission line 18 by means of conductor line 66, conductor line 68, resistor 70 and capacitor 72. A filter circuit comprised of capacitor 74 and resistor 76 is connected in parallel with the primary coil 64 of the transformer 66. The secondary coil 78 of this transformer has a conductor line 80 connected to it at its center point 82. Conductor line 80 is electrically coupled with output terminal 84 through a decoupling filter comprised of inductor 86 and capacitors 88 and 90.

The second bridge demodulator 44 is comprised of transformer 92, diodes 94, 96, 98 and 100, and resistors 102, 104, 106 and 108 and represents the phase detector circuit. Transformer 92 is provided with a primary coil 110 which is electrically coupled with transmission line 18 by means of conductor line 66, conductor line 112, and capacitor 114. A filter circuit comprised of resistor 116 and capacitor 118 is connected in parallel with primary coil 110. The secondary coil 120 of transformer 92 has a conductor line 122 connected to it at its center point 124. This conductor line is electrically coupled with the phase comparison output 126 through a decoupling filter comprised of inductor 128 and capacitors 130 and 132.

The overload sensing circuit is comprised of a pair of diodes 134 and 140 which are electrically coupled with transformer 36 by means of conductor lines 142 and 144. Diodes 134 and 140 are electrically coupled with the overload sense output terminal 146 by means of conductor lines 148, 150 and 152 and a decoupling filter comprised of inductor 154 and capacitors 156 and 158.

The sample and hold portion of sampler circuit 20 is shown in FIG. 3. As shown in FIG. 3, the sample and hold portion of current sampler 20 is basically comprised of two sample and hold circuits which are generally designated by the numerals 160 and 162. Sample and hold circuit 160 is basically comprised of a negative feedback loop which is made up of transconductance amplifier 164, FET transistor 166 and resistor 168. This negative feedback loop has a centering network 169 connected to it. This centering network is comprised of positive input terminal 176, ground terminal 178, variable resistor 180 and resistors 182 and 184. A voltage signal is introduced into the negative feedback loop at input pin 3 of the transconductance amplifier 164. Input pin 3 is electrically coupled with input terminal 188 by means of a filtering network comprised of inductor 190, resistors 192 and 194, and capacitors 196 and 198. Input terminal 188 is electrically coupled with output terminal 84 which is shown in FIG. 2. The output of transconductance amplifier 164 is also coupled with capacitor 200 by means of conductor line 202 and resistor 204.

Sample and hold circuit 162 is also comprised of a negative feedback loop which is made up of transconductance amplifier 170, FET transistor 172 and resistor 174. A calibrating network comprised of positive input terminal 206, negative input terminal 208, invariable resistor 210, and resistors 212, 214 and 216 is similarly connected to this feedback loop. Input pin 3 of transconductance amplifier 170 is electrically coupled with input terminal 222 through a filtering network comprised of inductor 224, resistors 226 and 228, and capacitors 230 and 232. The output of transconductance amplifier 170 is once again coupled with a capacitor 234 by means of a conductor line 236 and a resistor 238.

The sample and hold circuit is provided with a keying circuit which controls the time period during which the signals provided to input terminals 188 and 222 are sampled. The keying signal is provided at input terminal 240. This signal is sent from input terminal 240 to the emitter terminal of switching transistors 242 and 244 via resistor 246, diode 248, capacitor 250, inverter 252, and resistors 254 and 256 respectively. The collector of switching transistor 242 is electrically coupled with input pin 5 of transconductance amplifier 164 by means of conductor line 258. Similarly, the collector of switching transistor 244 is electrically coupled with input pin 5 of transconductance amplifier 170 by means of conductor line 260.

Negative feedback loop 160 is electrically coupled with an amplifying circuit by means of conductor line 262, calibrating network 264, resistor 266 and capacitor 268. This amplifying circuit is comprised of an operational amplifier 270 which is electrically coupled with output terminal 272 by means of resistor 274. Operational amplifier 270 is a stable high gain DC amplifier wherein the level of gain is controlled by the value of resistors 276 and 278.

The output of negative feedback loop 162 is also provided to an amplifying stage by means of conductor line 280, calibrating network 282, resistor 284 and conductor line 286. This amplifying stage is comprised of operational amplifier 300 which produces a gain determined by the values of resistors 302 and 304. The output of operational amplifier 300 is electrically coupled with the base of transistor 306 and the base of transistor 310 through diode 312. Biasing of these transistors is performed by capacitors 320, and resistors 314, 316 and 318. The emitter of transistor 306 and the emitter of transistor 310 are coupled to output terminal 322 through inductor 324 and capacitor 326.

Conductor line 286 has a shut-off circuit connected to it. This shut-off circuit is basically comprised of switching transistor 290 which is arranged to connect conductor line 286 to ground when this transistor is switched on. The switching state of this transistor is controlled by input terminal 292 which is electrically coupled to the digital controller and display circuit 26. Capacitor 294 and resistors 296 and 298 are provided to properly bias switching transistor 290.

Figure 4:
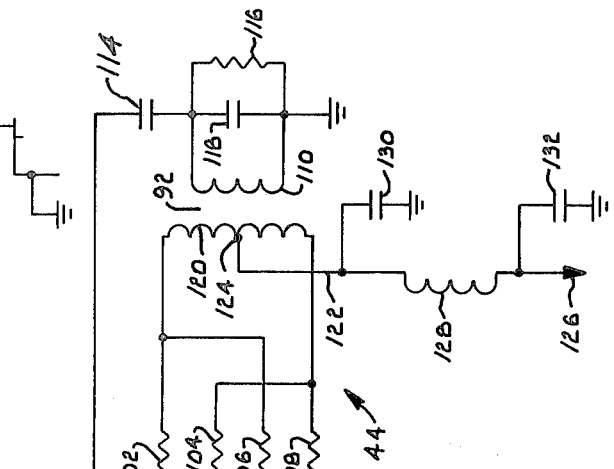
FIG. 4 is a schematic diagram of the overload detector portion of the sampler circuit shown in FIG. 1.

Referring now to FIG. 4, the overload detector circuit is shown in this figure. The overload detector is basically comprised of a voltage comparator 330. Voltage comparator 330 compares the voltage of the signal provided to input pin 2 with that of a reference signal which is provided to input pin 3. The voltage of the reference signal is set by a voltage divider comprised of power terminal 332, variable resistor 334 and resistors 336 and 338. The overload signal which is compared in voltage comparator 330 is inputted to this circuit at terminal 340. Input terminal 340 is electrically coupled with the overload sense output terminal 146 which is shown in FIG. 2. The overload sense signal is transmitted from input terminal 340 to input pin 2 of voltage comparator 330 through a filtering network comprised of inductor 342, capacitors 344 and 346, and resistors 348 and 350. The output of voltage comparator 330 is electrically coupled with output terminal 352 by means of resistor 354 and diode 356.

A detailed schematic diagram of the keying and computing circuit is shown in FIG. 5. As shown in FIG. 5, this circuit is provided with a set of input terminals 358, 360, 362, 364, 366, 368, 370 and 372 which accept a digital number representative of the duty cycle from the digital controller and display circuit 26. These input terminals are electrically coupled with a pair of latch elements 374 and 376. Latch 374 is electrically coupled with a digital comparator 378 by means of inverters 380, 382, 384 and 386. Latch 376 is similarly connected to a digital comparator 388 by means of inverters 390, 392, 394, and 396. The other set of inputs to digital comparators 378 and 388 are generated in a counting circuit 398 which is clocked by a timing signal provided to input terminal 400 from the digital controller and display circuit 26. This circuit provides at output pins 9, 7, 6, 5, 3, 2, 4 and 13 a digital number representative of the count state of this circuit. This digital number is simultaneously provided to digital comparators 378 and 388, to latch elements 402 and 404 through inverters 406, 408, 410, 412, 414, 416, 418 and 420 and to logic gate 421. Digital comparator 378 is arranged to generate a keying signal at output pin 5 as long as the digital number provided to input pins 10, 12, 13 and 15 of digital comparators 378 and 388 is greater than the digital number provided to input pins 1, 9, 11 and 14 of these comparators. The keying signal is provided to output terminal 422 by means of inverter 424, capacitor 426 and inductor 428.

The digital number representative of the duty cycle is also provided to an eight-bit multiplying digital-to-analog converter circuit 430. This circuit is a conventional integrated circuit such as the MC 3408 eight-bit multiplying digital-to-analog converter manufactured by Motorola Semi-Conductor Products, Inc. and is comprised of a reference current amplifier, an R-2R ladder, and 8 high speed current switches. The 8 high speed current switches provide at output pin 4 a current which is a linear product of the eight-bit digital word provided to input pins 5, 6, 7, 8, 9, 10, 11 and 12 and the analog voltage signal provided to input pin 14. Input pin 14 is electrically connected to input terminal 432 which is coupled with output terminal 272 of the sample and hold circuit shown in FIG. 3.

The current signal outputted at pin 4 of the eight-bit multiplying digital-to-analog converter circuit 430 is provided to an analog-to-digital converter through a decoupling amplifier 434. While the analog-to-digital converter can be made from any one of a number of well known designs, the one used in this embodiment of the invention is comprised of an MC 3408 eight-bit multiplying digital-to-analog converter generally designated by the number 436 and a voltage comparator 438. The reference voltage provided to input pin 2 is generated by power terminal 440 in combination with resistors 442, 444 and 446. The output of the voltage comparator is electrically coupled with the input pins of flip flop 448.

Flip flop 448 is also coupled with logic gate 421 through an inverter 451. Input pin 3 of flip flop 448 is electrically connected with input terminal 450 while the set output at pin 1 is electrically connected to latch elements 402 and 404 by means of conductor line 452. Flip flop 448 is electrically connected to latch elements 402 and 404 such that the presence of a positive voltage signal at output pin 1 causes the digital number provided to input pins 11, 12, 13 and 14 of the latch elements to be strobed into these elements. Latch elements 402 and 404 are also coupled with output terminals 454, 456, 458, 460, 462, 464, 466 and 468.

Output pin 14 of the counting circuit of 398 is electrically coupled with flip flop 470 while output pin 1 is electrically coupled with a second counting circuit 472. Output pin 3 of counting circuit 472 is electrically coupled with a second flip flop 474. Flip flops 470 and 474 are electrically coupled with output terminals 476 and 478 respectively.

Referring now to FIG. 6, the applicator head is schematically illustrated in this figure. As shown in FIG. 6, the applicator head includes an induction coil 500 which generates RF energy in response to a high frequency current flow through this electrode. The induction coil 500 has an electrostatic shield 502 interpositioned between it and its attendant load and a capacitor 504 connected in parallel with it. A variable capacitor 506 is provided to keep the applicator head tuned in electrical resonance. This variable capacitor is controlled by a servo motor which is not shown in this figure. The applicator head is connected to the transmission line 18 by means of a pi matching network which is comprised of a capacitor 508 and a pair of inductors 510 and 512.

In operation, the desired power setting and time period of activation is preset into the digital controller and display circuit 26. The power setting is a figure expressed in watts which represents the amount of power to be absorbed by the load. The time period of activation is the selected period of time during which the diathermy apparatus is to be activated. This time period is variable with the length of time being selected in accordance with the type of treatment for which the diathermy apparatus is to be used. Additional information may also be programmed into the digital controller and display circuit in accordance with the sophistication of the particular diathermy apparatus. Upon activation of the diathermy apparatus, the digital controller and display circuit 26 sends a digital number representative of the duty cycle to the keying and computing circuit 28. The initial duty cycle is of a standard minimum duration.

Referring now to FIG. 5, the digital number representative of the duty cycle is accepted by the computing and keying circuit 28 via input terminals 358, 360, 362, 364, 366, 368, 370 and 372. The digital number representative of the duty cycle is stored in latch elements 374 and 376 from which it is simultaneously provided to input pins 10, 12, 13 and 15 of digital comparators 378 and 388 and input pins 5, 6, 7, 8, 9, 10, 11 and 12 of the eight-bit multiplying digital-to-analog converter circuit 430.

Upon activation of the diathermy apparatus, a clock signal is provided to counting circuit 398 from the digital controller and display circuit 26 via input terminal 400. Counting circuit 398 has a maximum count state equal to the duration of the repetition period. The counting operation of this circuit is continuous with the counting circuit automatically being reset to zero when its maximum value is obtained. In the preferred embodiment of the invention, the clock signal provided to input terminal 400 has a frequency of 127.5 khz which causes counting circuit 398 to count to its maximum state 500 times per second. In this way, a repetition period corresponding to 1/500 of a second is established. As counting circuit 398 counts up to its maximum value, it outputs at output pins 2, 3, 4, 5, 6, 7, 9 and 13 a digital number equal to its present count state. This number is then provided to input pins 1, 9, 11 and 14 of the digital comparators 378 and 388; to input pins 11, 12, 13 and 14 of latch elements 402 and 404; and to input pins 5, 6, 7, 8, 9, 10, 11 and 12 of the eight-bit multiplying digital-to-analog converter 436.

Digital comparators 378 and 388 are arranged to generate a keying signal at output pin 5 of the digital comparator 378 as long as the digital number provided to input pins 10, 12, 13 and 15 is greater than or equal to the digital number provided to input pins 1, 9, 11 and 14. In other words, the keying signal is generated as long as the digital number representative of the duty cycle is greater than or equal to the count state of counting circuit 398. In this way, a keying signal having a duration which corresponds to the duty cycle is generated during each repetition period. This keying signal is provided from output terminal 422 to the RF power amplifier via the key line shown in FIG. 1. Output terminal 422 is also coupled with input terminal 240 shown in FIG. 3.

The application of a keying signal to the RF power amplifier keys on this circuit causing the high frequency electric currents generated by this circuit to be sent to the inductive coil within the applicator head. The inductive coil generates electrostatic and electromagnetic energy in response to these high frequency electric currents. This RF energy is then controllably applied to the body of the patient by the applicator head. In the preferred embodiment of the invention, the applicator head is equipped with an electrostatic shield which significantly attenuates the electrostatic energy generated by the inductive coil within the head. Attenuation of the electrostatic energy significantly enhances the stability of the diathermy apparatus by eliminating capacitive coupling between the applicator head and the body of the patient. The electrostatic shield allows the generated electromagnetic energy to pass through it unimpeded so that the deep heating action of the diathermy apparatus is not affected.

The level of power being absorbed by the treated body tissue is ascertained by using the sampling circuit shown in FIG. 2 to measure the current being provided to the applicator head. Current is measured by current transformer 36 which develops a voltage proportional to the measured current across resistors 38 and 40. Current transformer 36 is a half-wave length away from the induction coil in the applicator head so that the current measured by this transformer is proportional to the current being provided to the applicator head.

The voltage produced across resistors 38 and 40 is then rectified in bridge demodulator 42 to provide at output terminal 84 a DC voltage signal representative of the amplitude of the measured current. Bridge demodulator 42 acts as a double pole double throw switch which operates as a demodulator. The demodulator has two switching states during which one of two circuit paths is closed. The first circuit path is made up of diode 38, resistor 56, secondary coil 78, resistor 62 and diode 54 while the second circuit path is comprised of diode 52, resistor 60, secondary coil 78, resistor 58 and diode 50. The demodulator is switched between these two states at a frequency equal to that of the voltage signal picked off of transmission line 18 by conductor line 66. The voltage signal is picked off of transmission line 18 by conductor line 66 and is then sent to the primary coil 64 of transformer 46 by means of conductor line 68, resistor 70, and capacitor 72. A filtering network comprised of capacitor 74 and resistor 76 is provided to remove any RF that may accompany the voltage signal. The voltage signal is provided to the primary coil unchanged so that the phase and frequency of this signal is equal to that of the measured current. Therefore, demodulator 42 acts as a rectifying circuit which provides at output terminal 84 a DC voltage signal representative of the amplitude of the measured current.

Bridge demodulator 44 acts as a phase detector which produces a DC signal having a voltage related to the phase difference between the voltage and current being provided to the applicator head. Bridge demodulator 44 operates in the same manner as bridge demodulator 42 with the exception that the voltage signal provided to the primary coil 110 of transformer 92 is shifted in phase by 90°. By shifting the phase of the voltage signal by 90°, demodulator 44 produces at output terminal 126 a phase comparison signal which is a DC voltage signal representative of the phase difference between the voltage and current being provided to the applicator head. If the voltage and current are in phase, the phase comparison signal is zero. However, if the voltage and current are not in phase, the phase comparison is varied accordingly.

The current sampling circuit shown in FIG. 2 is also provided with an overload sensing circuit which measures current independent of voltage. The overload sensing circuit is comprised of diodes 134 and 140 which are electrically coupled with output terminal 146 via a decoupling filter comprised of inductor 154 and capacitors 156 and 158. The overload sensing circuit measures current independent of voltage so that this circuit will provide an overload sense signal if the applicator head becomes overloaded.

Referring now to FIG. 3, the DC voltage signal representative of the amplitude of the measured current and the phase comparison signal are provided to sample and hold circuits 160 and 162 via input terminals 188 and 222 respectively. Sample and hold circuits 160 and 162 respectively sample the incoming DC voltage signal representative of current and the phase comparison signal during the duty cycle and retain a voltage equal to that of the sampled signal until these signals are once again sampled during the next duty cycle. The sample and hold circuits are keyed on by a keying circuit which is comprised of input terminal 240, diode 248, capacitor 250, switching transistors 242 and 244, and resistors 246, 254 and 256. Input terminal 240 is electrically coupled with output terminal 422 (shown in FIG. 5) so that the keying circuit is activated only during the duty cycle. The keying circuit is electrically coupled with input pin 5 of transconductance amplifier 164 and input pin 5 of transconductance amplifier 170 to initiate the sampling operation of these circuits when the keying circuit is activated.

As mentioned above, sample and hold circuit 160 samples and holds the DC voltage signal representative of the amplitude of the measured current while sample and hold circuit 162 samples and holds the phase comparison signal. Since both of these sample and hold circuits operate in exactly the same manner, only the operation of sample and hold circuit 160 will be described in detail herein.

The DC voltage signal representative of the amplitude of the measured current is provided to sample and hold circuit 160 at input terminal 188. This signal is then sent to input pin 3 of transconductance amplifier 164 through a filtering network comprised of inductor 190, resistors 192 and 194, and capacitors 196 and 198. When the transconductance amplifier is keyed on by the presence of a keying signal at input pin 5, FET transistor 166 provides an output signal on conductor line 501. This output signal is fed back to input pin 2 of transconductance amplifier 164 to form a negative feedback loop which causes the sample and hold circuit to acquire a voltage equal to that of the DC voltage signal provided to input pin 3. It should be pointed out that transconductance amplifier 164 is only conducting when it is keyed on so that the incoming DC voltage signal representative of the amplitude of the measured current is only sampled during the duty cycle.

The output of transconductance amplifier 164 is also coupled with capacitor 200 by means of conductor line 202 and resistor 204. By connecting capacitor 200 to the output of transconductance amplifier 164, a charge representative of the peak voltage over the duty cycle is stored on this capacitor when the transconductance amplifier is conducting. When transconductance amplifier 164 is not keyed on, its output terminal presents a high impedance causing the charge stored on capacitor 200 to be retained. In this way, the voltage on conductor line 501 is maintained at the value of the peak sampling voltage signal.

The voltage signal on conductor line 501 is also sent by means of conductor line 262 to operational amplifier 270 through a calibrating device comprised of variable resistor 264 and a filter network comprised of resistor 266 and capacitor 268. Operational amplifier 270 is a high gain stable amplifier which amplifies the incoming signal by an amount determined by the value of resistors 276 and 278. The amplified signal is then sent to output terminal 272 and represents the above mentioned current sample signal.

Sample and hold circuit 160 automatically adjusts the sampled voltage signal to account for the amount of head loss at any particular power level so that the current sample signal provided at output terminal 272 is an accurate representation of the level of power actually being absorbed by the load. This adjustment is performed by subtracting the known amount of head loss at the particular power level from the sampled voltage signal. This operation is accomplished within the sample and hold circuit by properly setting centering circuit 169 and the calibrating device comprised of variable resistor 264 as will be described in greater detail herein.

As mentioned above, sample and hold circuit 162 operates in exactly the same manner as sample and hold circuit 160. Therefore, sample and hold circuit 162 produces on conductor line 280 a voltage signal having a value equal to the voltage of the phase comparison signal provided to input pin 3 of transconductance amplifier 170. This voltage signal is passed through a calibrating device comprised of variable resistor 282 and is then provided to input pin 5 of operational amplifier 300 via conductor line 286. Conductor line 286 is also connected to ground through switching transistor 290. When the diathermy apparatus is shut off, a termination signal is provided to input terminal 292 from the digital controller and display circuit 26. The presence of a termination signal at input terminal 292 causes switching transistor 290 to saturate thereby directing the voltage signal on input line 286 to ground rather than to operational amplifier 300.

Operational amplifier 300 is a high gain operational amplifier which amplifies the incoming signal by an amount determined in accordance with the value of resistors 302 and 304. The amplified signal is then provided to the base of transistors 306 and 310. These transistors act as amplifiers which further amplify the sampled signal. The amplified voltage signal present at output terminal 322 is used to control a servo motor which is not shown in FIG. 3. This servo motor controls a tuning element in the applicator head to maintain the head in electrical resonance thereby maintaining a zero phase angle between the voltage and current.

Referring now to FIG. 4, the overload sense signal is provided to input terminal 340 of the overload detector circuit shown in this figure. The overload sense signal provided to input terminal 340 is sent to input pin 2 of voltage comparator 330 through a filtering network comprised of inductor 342, capacitors 344 and 346, and resistors 348 and 350. Voltage comparator 310 compares the voltage signal provided to input pin 2 with a reference voltage provided to input pin 3. The reference voltage is set by a voltage divider comprised of power terminal 332, variable resistor 334, and resistors 336 and 338. The variable resistor 334 is adjusted until a desired level of voltage is provided to input pin 3. If the voltage provided to input pin 2 exceeds the reference voltage due to an overload condition, voltage comparator 330 generates an overload signal. This overload signal is then sent to the digital controller and display circuit by means of output terminal 352. In response to an overload signal, the digital controller and display circuit automatically terminates the operation of the diathermy apparatus.

Returning now to FIG. 5, the figure representative of the total amount of power being absorbed by the load is derived in this circuit by multiplying the duty cycle by the current sample signal. The current sample signal is multiplied by the duty cycle in the eight-bit multiplying digital-to-analog converter 430. The digital number representative of the duty cycle is provided to input pins 5, 6, 7, 8, 9, 10, 11 and 12 from latch elements 374 and 376. The current sample signal is sent to input pin 14 from the sample and hold circuit shown in FIG. 3 through input terminal 432. The eight-bit multiplying digital-to-analog converter circuit 430 multiplies the digital number representative of the duty cycle by the current sample signal and generates at output pin 4 a current signal which is the linear product of these two values. The current signal which is the linear product of the duty cycle and current sample is then sent to an analog-to-digital converter through decoupling amplifier 434. The analog-to-digital converter is comprised of another eight-bit multiplying digital-to-analog converter 436 and a voltage comparator 438. The eight-bit multiplying digital-to-analog converter 436 receives at input terminals 5, 6, 7, 8, 9, 10, 11 and 12 a digital number from counting circuit 398. Since the analog input of this circuit is connected to ground, the output current is proportional only to the digital number provided to this circuit. As the digital number increases, the voltage at output pin 4 rises an incremental amount. When the voltage from the eight-bit multiplying digital-to-analog converter 436 becomes equal to the voltage representative of total power, voltage comparator 438 is tripped causing it to generate a set signal. This set signal is then sent to flip flop 448 where it causes this flip flop to be set thereby producing a strobe signal at output pin 1. The strobe signal is provided to latch elements 402 and 404 causing the digital number at input pins 11, 12, 13 and 14 of latch element 402 and at input pins 11, 12, 13 and 14 of latch element 404 to be strobed into these storage elements. The digital number is thus stored until the strobe signal is removed by resetting flip flop 448. If flip flop 448 is not set before the count state of counting circuit 398 reaches 255, logic gate 421 sets this flip flop by providing a logic signal to input pin 6 of flip flop 448 through inverter 451. This logic signal sets flip flop 448 causing the digital number 255 to be stored in latch elements 402 and 404. Flip flop 448 is reset by the digital controller and display circuit after the digital number representative of total power is provided to this circuit via output terminals 454, 458, 460, 462, 464, 466 and 468.

Counting circuits 398 and 472 operate in combination to produce a clock signal at output pin 3 about 100 times a second. This clock signal is provided to the set input of flip flop 474 causing a read signal to be generated at output pin 478. This read signal indicates to the digital controller and display circuit that it is time to take a power reading. In response to this read signal, the digital controller and display circuit accepts the digital number representative of the total power from the keying and computing circuit. Once the digital number representative of total power has been received, the digital controller and display resets flip flop 448 and flip flop 474. Counting circuit 398 also provides a clock signal at output pin 14 once every second. This clock signal is provided to the said input of flip flop 470 which controls the timer in the digital controller and display circuit. The digital number representative of total power is compared with the preset level of power and the duration of the duty cycle is adjusted accordingly.

It should be pointed out at this time that the digital number provided at output pins 454, 456, 458, 460, 462, 464, 466 and 468 accurately represents the amount of power actually being absorbed by the load because sample and hold circuit 160 automatically adjusts for the amount of head loss at any particular power level once this circuit is properly centered and calibrated. The sample and hold circuit is centered and calibrated by performing the centering and calibration adjustments described herein. The calibration adjustment varies the power measurement to adjust for the amount of head loss produced when a load is within the radiating region of the applicator head. This adjustment is made by means of the calibrating device comprised of variable resistor 264. The centering adjustment, on the other hand, adjusts the power measurement to account for the amount of head loss which is present within the applicator head when the head is unloaded. This adjustment is performed in centering circuit 169.

To make the above mentioned calibration and centering adjustments, a bridge or vector impedance meter is used to measure the maximum and minimum impedance of the applicator head while the head is maintained in electrical resonance. This information is then used to calculate the amount of head loss at a particular reference wattage. As described above, the amount of head loss at this wattage level is equal to the reference wattage times the ratio between the maximum and minimum impedance. Thereafter, the applicator head is replaced by a non-inductive reference load having a resistance which is capable of dissipating the reference wattage over the entire duty cycle. The reference load is connected to the transmission line such that the electrical distance between this load and the sample circuit 20 is exactly equal to a half wave length. An in-line watt meter is also connected in series with the reference load to measure the level of power being applied to the load. The diathermy apparatus is then activated and the reference wattage is set into the apparatus. The calibration adjustment is then made by adjusting the calibrating device comprised of variable resistor 264 until the digital number representative of power is equal to the reference wattage and the in-line watt meter indicates that the level of power being provided to the reference load is equal to the sum of the reference wattage and the amount of head loss computed for this level of power.

Once the calibration adjustment is completed, the reference load is removed and the applicator head is once again connected to the diathermy apparatus. The reference wattage is then applied to the applicator head while the head is maintained in an unloaded condition. When the head is unloaded any power dissipation is a result of the inherent loss of the applicator head. To account for this head loss, the centering adjustment is performed by adjusting the centering circuit 169 until the digital number representative of power is equal to zero.

This centering adjustment may cause a slight change in the calibration adjustment. As a result, the calibration adjustment must be checked once again by replacing the applicator head with the reference load and allowing the reference wattage to be applied to this load. The digital reading representative of the power load and the reading on the in-line watt meter are then checked to determine if the device is still properly calibrated. The device is properly calibrated if the digital number representative of power is equal to the reference wattage while the reading on the in-line watt meter is still equal to the sum of the reference wattage and the amount of head loss computed for this power level. If these readings do not coincide, the above-mentioned calibration adjustment must be performed a second time.

Following this second calibration adjustment, the centering adjustment is once again checked to determine if the calibration adjustment has effected the centering adjustment. If it has, the centering adjustment is repeated. The calibration and centering adjustments are alternately performed in this manner until the sample and hold circuit is properly centered and calibrated. Once the diathermy apparatus is properly centered and calibrated, the sample and hold circuit automatically accounts for the amount of head loss at any particular power level.

From the foregoing, it will be seen that this invention is well adapted to attain all the ends and objects herein above set forth together with other advantages which are obvious and are inherent to the structure.

It will be understood that certain features and subcombinations are of utility and may be employed without reference to other features and subcombinations.

As many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A method for controlling the amount of power being absorbed by a load within the irradiating region of an applicator head of a shortwave diathermy apparatus, said method comprising the steps of
   selecting a power setting,
   periodically establishing a duty cycle of variable duration,
   generating a radio frequency electric signal during said duty cycle said radio frequency electric signal having a current component and a voltage component,
   providing said radio frequency electric signal to said applicator head to thereby produce electrostatic and electromagnetic energy in said applicator head,
   applying said electrostatic and electromagnetic energy to said load by means of said applicator head,
   ascertaining the level of power being absorbed by said load during the duty cycle to obtain a first power measurement,
   deriving from said first power measurement and the duration of the duty cycle a power figure representative of the amount of power being absorbed by said load,
   comparing said power figure with said power setting, and
   varying the duration of the duty cycle so as to reduce the difference between said power setting and said power figure.

2. The method as in claim 1 including the step of attenuating at least a portion of said electrostatic energy before said electrostatic energy reaches said load.

3. The method as in claim 1 including the step of restricting the amount of power being absorbed by said load to a preselected maximum by placing a maximum limit on the duration of the duty cycle.

4. The method as in claim 1 including the step of placing a maximum limit on said power figure.

5. The method as in claim 1 including the step of selecting a new power setting after a set period of time.

6. The method as in claim 1 wherein the step of ascertaining the level of power being absorbed by said load during the duty cycle comprises the steps of
   maintaining said applicator head in electrical resonance,
   measuring the level of power being provided to said applicator head during the duty cycle to obtain a second power measurement,
   determining the level of power dissipated in said applicator head to obtain head loss value, and
   adjusting said second power measurement to compensate for the level of power dissipated in said applicator head as head loss to obtain said first power measurement.

7. The method as in claim 6 wherein said step of maintaining the applicator head in electrical resonance comprises the steps of monitoring the phase relationship between said current component and said voltage component, placing a tuning element in said applicator head, said tuning element being arranged to vary the impedance of said applicator head, and adjusting said tuning element so as to eliminate any difference in phase between said current component and said voltage component.

8. The method as in claim 6 wherein said step of measuring the level of power being provided to said applicator head during the duty cycle to obtain a second power measurement comprises the step of measuring the level of said current component during the duty cycle.

9. The method as in claim 6 wherein said step of determining the level of power dissipated in said applicator head as head loss comprises the steps of ascertaining the maximum impedance of said applicator head to obtain a maximum impedance figure, ascertaining the minimum impedance of said applicator head to obtain a minimum impedance figure, and multiplying said second power measurement by the quotient resulting from the division of said minimum impedance figure by said maximum impedance figure.

10. The method as in claim 6 wherein said step of adjusting said second power measurement to compensate for the level of powwer dissipated in said applicator head as head loss comprises the step of subtracting said head loss value from said second power measurement to obtain said first power mesurement.

11. A method for controlling the amount of power being absorbed by a load within the irradiating region of an applicator head of a shortwave diathermy apparatus having a signal source for generating a radio frequency electric signal having a current component and a voltage component and means for providing said radio frequency electric signal to said applicator head to produce electrostatic and electromagnetic energy in said applicator head, said method comprising the steps of establishing a preselected power setting, periodically establishing a duty cycle having a variable duration, generating said radio frequency electric signal during said duty cycle, ascertaining the level of power being absorbed by said load during the duty cycle to obtain a first power measurement, deriving from said power measurement and the duration of the duty cycle a power figure representative of the amount of power being absorbed by said load, comparing said power figure with said power setting to produce an output indicative of the difference in said power figure and said power setting, and using said difference output to adjust the duration of said duty cycle to thereby make said power figure correspond with said power setting.

12. The method as in claim 11 wherein the step of ascertaining the level of power being absorbed by said load during the duty cycle comprises the steps of maintaining said applicator head in electrical resonance, measuring the level of power being provided to said applicator head during the duty cycle to obtain a second power measurement, determining the level of power dissipated in said applicator head to obtain head loss value, and adjusting said second power measurement to compensate for the level of power dissipated in said applicator head as head loss to obtain said first power measurement.

13. The method as in claim 12 wherein said step of maintaining the applicator head in electrical resonance comprises the steps of monitoring the phase relationship between said current component and said voltage component, placing a tuning element in said applicator head, said tuning element being arranged to vary the impedance of said applicator head, and adjusting said tuning element so as to eliminate any difference in phase between said current component and said voltage component.

14. The method as in claim 12 wherein said step of measuring the level of power being provided to said applicator head during the duty cycle to obtain a second power measurement comprises the step of measuring the level of said current component during the duty cycle.

15. The method as in claim 12 wherein said step of determining the level of power dissipated in said applicator head as head loss comprises the steps of ascertaining the maximum impedance of said applicator head to obtain a maximum impedance figure, ascertaining the minimum impedance of said applicator head to obtain a minimum impedance figure, and multiplying said second power measurement by the quotient resulting from the division of said minimum impedance figure by said maximum impedance figure.

16. The method as in claim 12 wherein said step of adjusting said second power measurement to compensate for the level of power dissipated in said applicator head as head loss comprises the step of subtracting said head loss value from said second power measurement to obtain said first power measurement.

17. A shortwave diathermy apparatus comprising:

control means for programming a preselected power setting representative of a preselected amount of power into said diathermy apparatus;

means for periodically establishing a duty cycle of variable duration;

means for generating a radio frequency electric signal during said duty cycle, said radio frequency electric signal having a current component and a voltage component;

head means for converting said radio frequency electric signal into electrostatic and electromagnetic energy and for applying said electrostatic and electromagnetic energy to a selected load;

means for ascertaining the level of power being absorbed by said load during said duty cycle, said ascertaining means being operable to provide a power measurement representative of the level of power being absorbed by said load during said duty cycle;

means for using said power measurement and the duration of the duty cycle to derive a power figure representative of the total amount of power being absorbed by said load;

means for comparing said power figure with said power setting; and means for varying the duration of the duty cycle so as to reduce the difference between said power figure and said power setting.

18. The apparatus as in claim 17 including means for changing the power setting after a selected period of time.

19. The apparatus as in claim 17 including means for controlling the time period during which said diathermy apparatus is operating.

20. The apparatus as in claim 17 including an electrostatic shield means for attenuating at least a portion of said electrostatic energy before said electrostatic energy reaches said load.

21. The apparatus as in claim 17 including means for coupling said head means to said generating means such that said head means experiences a maximum impedance when it is not loaded and a minimum impedance when it is fully loaded.

22. The apparatus as in claim 17 wherein said means for ascertaining the level of power being absorbed by said load during said duty cycle is comprised of means for maintaining said head means in electrical resonance; means for measuring the level of power being provided to said head means, said power measuring means being operable to provide an output indicative of said measured level of power; and means for translating said output into said power measurement.

23. The apparatus as in claim 22 wherein said means for maintaining said head means in electrical resonance is comprised of
means for monitoring the phase relationship between said current component and said voltage component, said monitoring means being operable to provide a phase control signal representative of the difference in phase between said current component and said voltage component,
a tuning element in said head means, said tuning element being arranged to vary the impedance of said head means, and
means for adjusting said tuning element in response to said phase control signal to thereby vary the impedance of said head means so as to eliminate any difference in phase between said current component and said voltage component.

24. The apparatus as in claim 23 wherein said monitoring means is comprised of
a current transformer means for sensing said current component to produce a current phase signal having a frequency and phase related to the frequency and phase of said current component, and
demodulator means for rectifying said current phase signal to provide said phase control signal in the form of a DC voltage signal having a voltage representative of the difference in phase between said current component and said voltage component.

25. The apparatus as in claim 24 wherein said demodulator means is comprised of a first circuit path and a second circuit path wherein each circuit path has a common input and a common output, said first circuit path presenting a barrier to negative current flow and said second circuit path presenting a barrier to positive current flow, said current phase signal being alternately introduced to said first circuit path and said second circuit path at a frequency which is 90° out of phase with said voltage signal to thereby produce at said output said phase control signal in the form of a DC voltage signal having a voltage representative of the difference in phase between said current component and said voltage component.

26. The apparatus as in claim 24 wherein said adjusting means is comprised of a servo motor having a forward and reverse direction said motor being controlled by said phase control signal.

27. The apparatus as in claim 22 wherein said means for measuring the level of power being provided to said head means is comprised of current measuring means for measuring the level of said current component.

28. The apparatus as in claim 27 wherein said current measuring means is comprised of a current transformer means for sensing said current component to produce a current sample signal representative of the level of said current component.

29. The apparatus as in claim 28 wherein said means for translating said output into said power measurement is comprised of a demodulator means for rectifying said current sample signal to provide said power measurement in the form of a DC voltage signal having a voltage related to the amplitude of said current component.

30. The apparatus as in claim 29 wherein said demodulator means is comprised of a first circuit path and a second circuit path wherein each circuit path has a common input and a common output, said first circuit path presenting a barrier to negative current flow and said second circuit path presenting a barrier to positive current flow, said current sample signal being alternately introduced to said first circuit path and said second circuit path at a frequency which is in phase with said voltage component to thereby produce at said output said power measurement in the form of a DC voltage signal having a voltage related to the amplitude of said current component.

31. The apparatus as in claim 29 including means for producing a digital signal representative of the duration of said duty cycle.

32. The apparatus as in claim 31 wherein said means for deriving a power figure is comprised of means for multiplying said digital signal by said power measurement, said multiplying means being operable to produce an analog signal representative of the product of said digital signal and said power measurement and means for converting said analog signal into said power figure.

33. The apparatus as in claim 17 including means for producing a figure representative of the duration of the duty cycle.

34. The apparatus as in claim 33 wherein said means for deriving a power figure from said power measurement and the duration of the duty cycle is comprised of means for multiplying said power measurement by said figure representative of the duration of the duty cycle.

35. The apparatus as in claim 17 including means for producing a voltage signal which is related to the level of said current component and means for producing an overload signal whenever the voltage of said voltage signal excludes a preselected level.

36. The apparatus as in claim 35 including means for inhibiting the generation of said radio frequency electric signal in response to said overload signal.

* * * * *